United States Patent [19]

Taylor et al.

[11] Patent Number: 5,458,105

[45] Date of Patent: Oct. 17, 1995

[54] WRIST WORN ANTI-SNORE APPARATUS FOR DETECTING SNORING AND FOR PRODUCING VIBRATORY MOTION

[75] Inventors: Charles E. Taylor, San Rafael, Calif.; Blaine M. Smith, Lincoln City, Oreg.

[73] Assignee: The Sharper Image Corporation, San Francisco, Calif.

[21] Appl. No.: 132,384

[22] Filed: Oct. 6, 1993

[51] Int. Cl.[6] .................................................. A61F 5/56
[52] U.S. Cl. ................................ 128/848; 340/575
[58] Field of Search ........................ 128/848; 340/575, 340/573

[56] References Cited

U.S. PATENT DOCUMENTS

| | | | |
|---|---|---|---|
| 3,089,130 | 5/1963 | Wilson | 340/279 |
| 3,434,470 | 3/1969 | Strickland | 128/136 |
| 3,462,777 | 8/1969 | Lutsky | 5/345 |
| 3,480,010 | 11/1969 | Crossley | 128/132 |
| 3,998,209 | 12/1976 | Macvaugh | 128/1 R |
| 4,093,944 | 6/1978 | Muncheryan . | |
| 4,120,299 | 10/1978 | Russo | 128/140 N |
| 4,536,905 | 8/1985 | DeSantis | 5/43 |
| 4,644,330 | 2/1987 | Dowling | 340/575 |
| 4,694,839 | 9/1987 | Timme . | |
| 4,715,367 | 12/1987 | Crossley | 128/136 |
| 4,941,478 | 7/1990 | Takeuchi et al. | 128/848 |
| 5,056,534 | 10/1991 | Wright | 128/848 |
| 5,081,447 | 1/1992 | Echols . | |
| 5,117,816 | 6/1992 | Shapiro et al. | 128/200.24 |
| 5,123,425 | 6/1992 | Shannon, Jr. et al. | 128/200.24 |
| 5,181,504 | 1/1993 | Ono et al. | 128/36 |

FOREIGN PATENT DOCUMENTS

| | | | |
|---|---|---|---|
| 168740 | 1/1986 | European Pat. Off. | A61F 5/56 |
| 0171321 | 2/1986 | France | 128/848 |
| 2651120 | 3/1991 | France | 128/848 |
| 3018336 | 11/1981 | Germany | 128/848 |
| 3801819 | 9/1989 | Germany | 128/848 |
| 2005862 | 4/1989 | Spain | A61F 5/56 |
| 8404159 | 6/1986 | Sweden | A61F 5/56 |
| 0358878 | 9/1931 | United Kingdom | 128/848 |
| 2208003 | 2/1989 | United Kingdom | A61F 5/56 |
| 8762577 | 5/1987 | WIPO | 128/848 |

OTHER PUBLICATIONS

"Photographs of SAVA International/Hamburg West Germany, Snore–No–More Device", Dec. 1993, Exhibits 1–23.
SAVA International/Hamburg West Germany, "Snore–No–More Instruction Manual", date unknown, all pages.
SAVA International/Hamburg West Germany, "Snore–No–More Package Illustrations", date unkown, all pages.

Primary Examiner—Robert A. Hafer
Assistant Examiner—Michael O'Neill
Attorney, Agent, or Firm—Flehr Hohbach, Test, Albritton & Herbert

[57] ABSTRACT

An anti-snore apparatus and method of stopping a person from snoring are disclosed. A preferred embodiment of the apparatus includes a housing that is wearable on a person's limb and a strap for securing the housing to a person's limb. Means are contained within the housing for receiving a power supply. A motor is secured to and contained within the housing. A weight is secured to an output shaft of the motor. The output shaft extends through the weight at a point outside of a center of gravity of the weight so that rotation of the weight by the output shaft produces a vibratory motion in the housing. A microphone is contained within the housing for detecting audible snoring and for producing a microphone output signal in response to such detected snoring. An audio amplifier amplifies the microphone output signal to produce an amplified microphone output signal. A comparator produces a comparator output signal in response to the amplified microphone output signal exceeding a predetermined level. An oscillator, responsive to the comparator output signal, generates an oscillator output signal characterized by a plurality of voltage pulses for switching the motor on and off a plurality of times.

7 Claims, 10 Drawing Sheets

WRIST WORN ANTI-SNORE APPARATUS FOR DETECTING SNORING AND FOR PRODUCING VIBRATORY MOTION

BACKGROUND OF THE INVENTION

1. Field of the Invention

The present invention relates to anti-snore devices, and, more particularly, to a wrist-worn anti-snore apparatus and method which detects the sound of a snore and provides a vibrating motion to the person's wrist to stop the person from snoring.

2. Description of the Related Art

There have been several attempts to eliminate snoring by using various electronic devices. Examples of such devices can be found in U.S. Pat. Nos. 4,715,367 to Crossley, 4,644,330 to Dowling, 3,998,209 to Macvaugh, and 3,480,010 to Crossley.

The '367 and '010 patents to Crossley describe devices that detect snoring and then induce a high voltage across two electrodes positioned on a sleeping person's neck. The high voltage is intended to shock the person and to condition the person to sleep without snoring. These devices suffer from the disadvantage that several high voltage shocks can eventually irritate, or even burn, the portion of the person's skin that is in contact with the electrodes.

The '330 patent to Dowling describes a device that is worn in the outer ear or attached to the ear of a sleeping person. A miniature microphone detects snoring sounds and then an aversive audio signal is emitted via a speaker into the person's ear. This device suffers from the disadvantage that ear-worn devices are often uncomfortable, and furthermore, ear-worn devices can be dangerous because they tend to impair the person's hearing such that the person unable to hear emergency devices, such as fire alarms.

The '209 patent to Macvaugh describes a device having an arm cuff that includes a vibratory electromagnet device having a clapper and a pair of electrodes. This device suffers from the disadvantage that there is one set of wires connecting the arm cuff to a separate control console and another set of wires connecting the control console to a separate microphone. A person can become easily tangled in the arm cuff wires which can disturb sleep, and the separate component configuration of the device make operation confusing and difficult.

Thus, there is a need for an anti-snore apparatus and method which overcomes the disadvantages of the above described devices.

SUMMARY OF THE INVENTION

The present invention provides an anti-snore apparatus that includes a housing that is wearable on a person's limb and means for securing the housing to a person's limb. The housing contains means for receiving a power supply. Vibrating means are contained within the housing for vibrating the housing. A microphone is contained within the housing for detecting audible snoring. Activation means are contained within the housing and responsive to the microphone for activating the vibrating means when the detected audible snoring has exceeded a predetermined level.

The present invention also provides a method of stopping a person from snoring. The method includes the steps of detecting a person's audible snoring, determining whether the audible snoring exceeds a predetermined level, and applying a vibratory motion to one of the person's limbs if the audible snoring exceeds the predetermined level.

A better understanding of the features and advantages of the present invention will be obtained by reference to the following detailed description of the invention and accompanying drawings which set forth an illustrative embodiment in which the principles of the invention are utilized.

DETAILED DESCRIPTION OF THE PREFERRED EMBODIMENTS

Referring to FIGS. 1 through 4, there is illustrated an anti-snore apparatus 20 in accordance with the present invention that is designed to stop a sleeping, snoring person from snoring. The apparatus 20 may be worn on the wrist 22 of a person 24 who is known to snore when he or she sleeps. All of the electrical components of the apparatus 20 are contained within a housing 32. The housing 32 includes a bottom cabinet 26, a top cabinet 28, a battery door 30, and two side covers 31. Because the apparatus 20 is self-contained, no external wires are required to connect the apparatus 20 to a central control console. The housing 32 preferably has a configuration and is made from a material that is wearable on the person's wrist 22, arm, or other limb. In other words, the housing 32 is preferably not too heavy or bulky and does not have sharp edges. The housing 32 is preferably made from ABS plastic.

The apparatus 20 is switched into operating mode by switching a switch cover 34 to the on position. In general, the apparatus 20 operates to stop the person 24 from snoring by detecting audible snoring via a microphone hole 36 in the housing 32. When the audible snoring exceeds a certain predetermined level, the housing 32 begins to vibrate. The vibrating motion of the housing 32 on the person's wrist 22 tends to disturb the person 24 without necessarily awakening him or her. This vibratory disturbance, which occurs each time the person's 24 audible snoring exceeds the predetermined level, will normally cause the person 24 to roll over or change sleeping positions which tends to cause the snoring to stop.

It is believed that a person snores most when sleeping on his or her back, and snoring is reduced or stopped when a person changes positions to sleep on his or her side or stomach. It is further believed that the vibratory motion of the apparatus 20 will "nudge" or cause the person 24 to change or roll to such a sleeping position where snoring will be either stopped or at least reduced. However, the person 24 does not necessarily have to change sleeping positions in order for the snoring to stop. The vibratory motion may cause the person to simply take a deep breath of air, swallow, cough, or the like, which can also cause the snoring to cease. It is even possible that the vibratory motion itself will stop the snoring. If the person 24 continues to snore and continually activates the vibratory motion of the apparatus 20, the person 24 will eventually awaken, in which case the snoring will be stopped.

The apparatus 20 indirectly improves the quality of sleep of another person or other people that may be trying to sleep in the same room or bed as the snoring person 24. Specifically, by stopping the person 24 from snoring, the other person or people will have a quieter environment in which to sleep. Therefore, the apparatus 20 serves the dual purpose of stopping the person 24 from snoring and improving the quality of other people's sleep.

Figure 1:
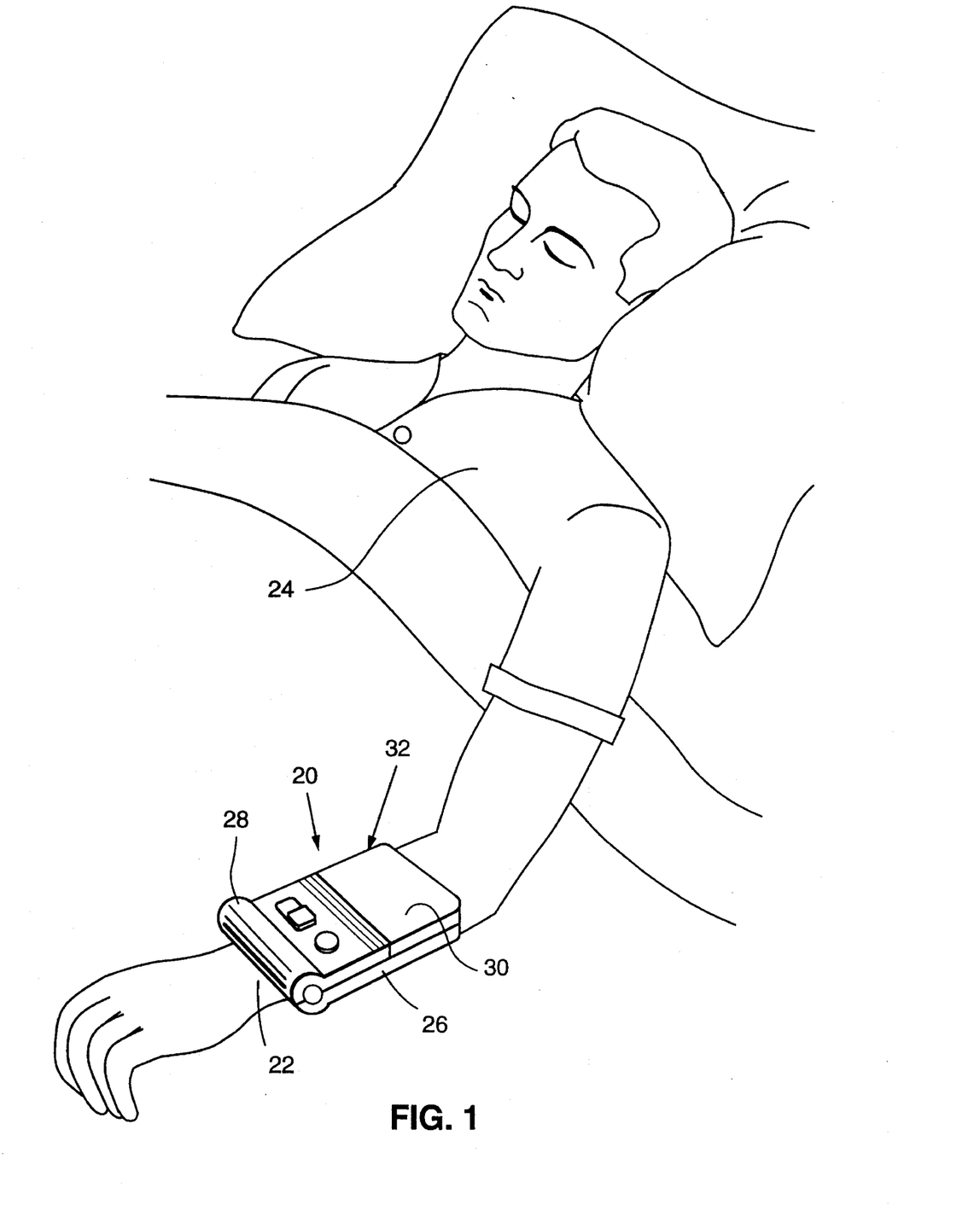
FIG. 1 is a perspective view of a sleeping person wearing an anti-snore apparatus in accordance with the present invention.
Figure 2:
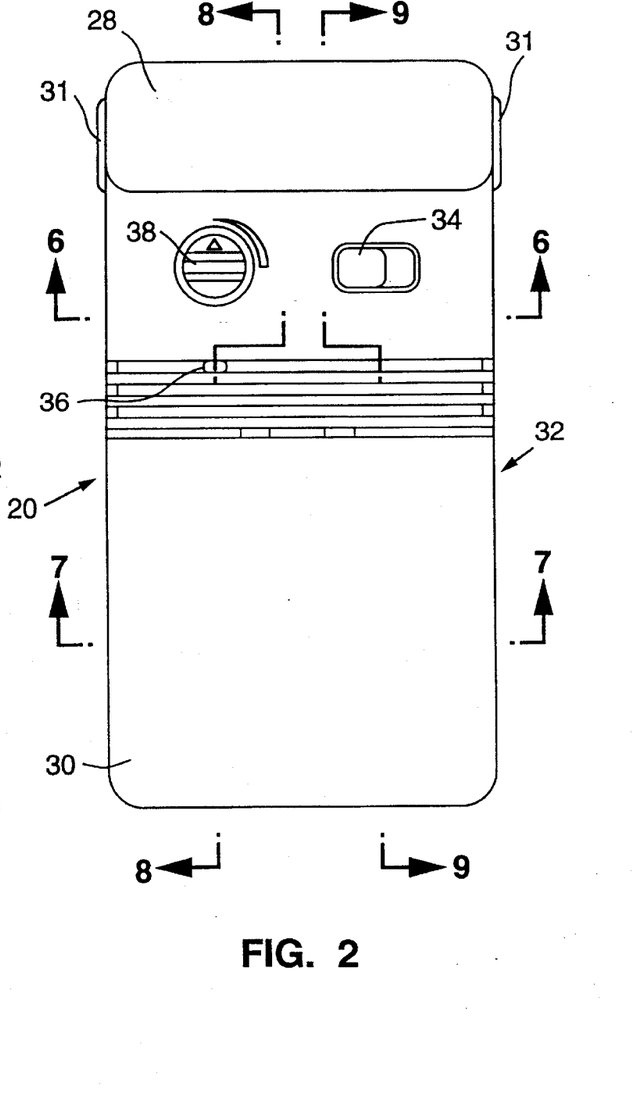
FIG. 2 is a front view of the anti-snore apparatus shown in FIG. 1.
Figure 3:
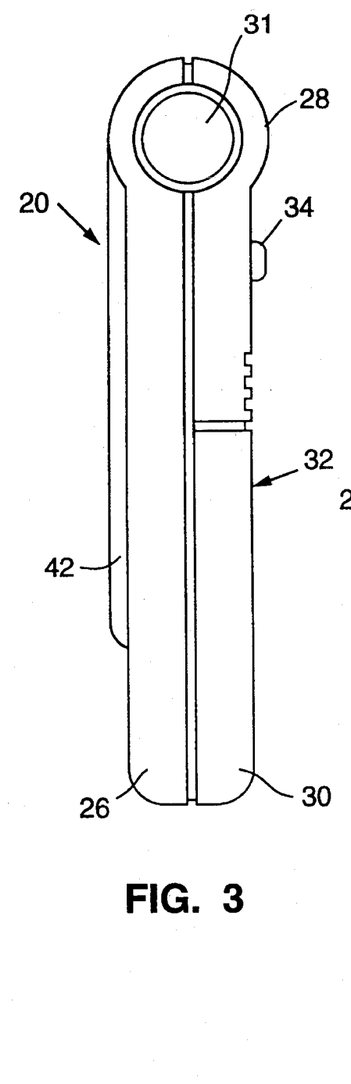
FIG. 3 is a side view of the anti-snore apparatus shown in FIG. 1.
Figure 4:
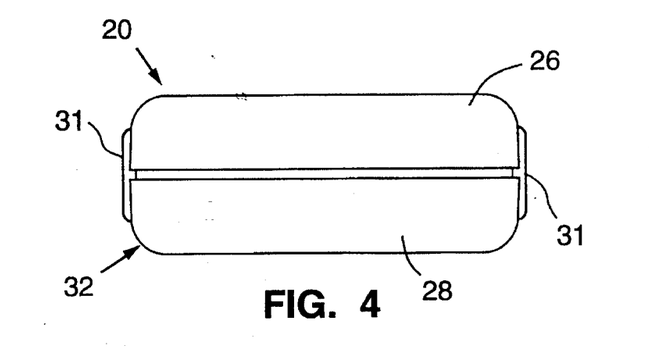
FIG. 4 is a top view of the anti-snore apparatus shown in FIG. 1.

A sensitivity control 38 adjusts the sensitivity of the apparatus 20. In other words, the sensitivity control 38 adjusts the predetermined level of snoring that will activate the vibratory motion of the apparatus 20. The sensitivity control 38, as well as the strength, length of time, and intervals of vibration produced by the apparatus 20, will be discussed in detail below.

Figure 5:
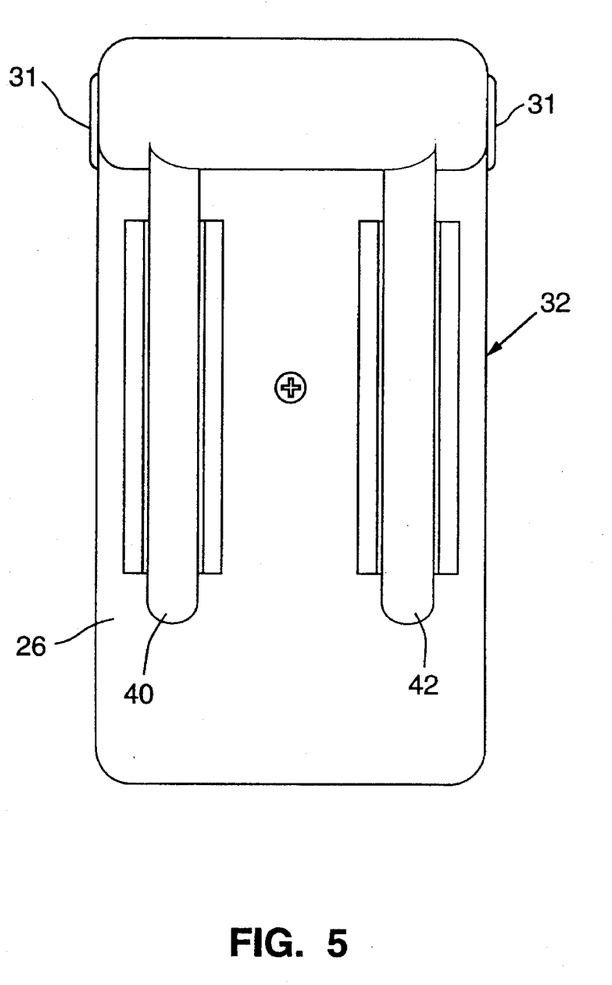
FIG. 5 is a rear view of the anti-snore apparatus shown in FIG. 1.
Figure 6A:
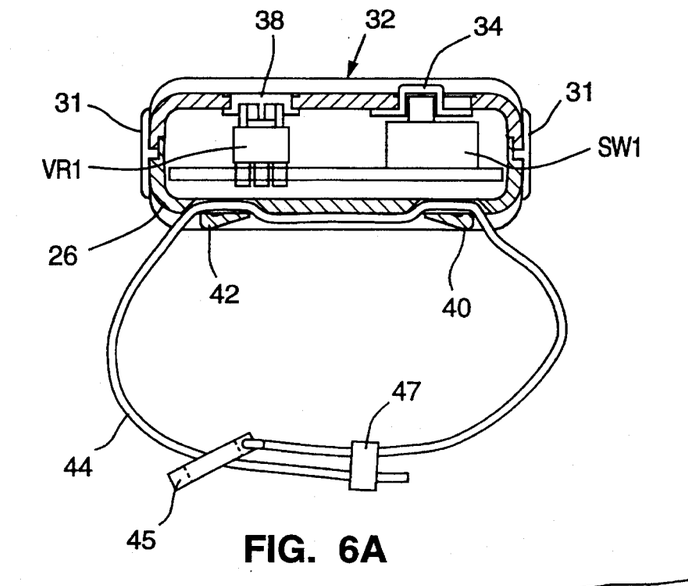
FIG. 6A is a cross-sectional view of the anti-snore apparatus shown in FIG. 2 taken along line 6—6 with the addition of a strap.
Figure 6B:
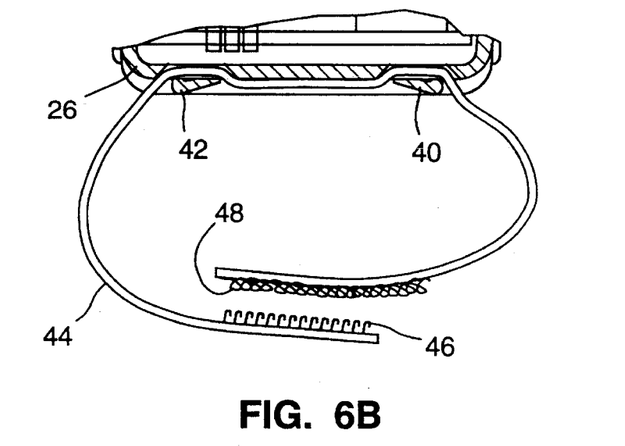
FIG. 6B is a partial cross-sectional view of the anti-snore apparatus shown in FIG. 2 taken along line 6—6 with the addition of a strap.
Figure 7:
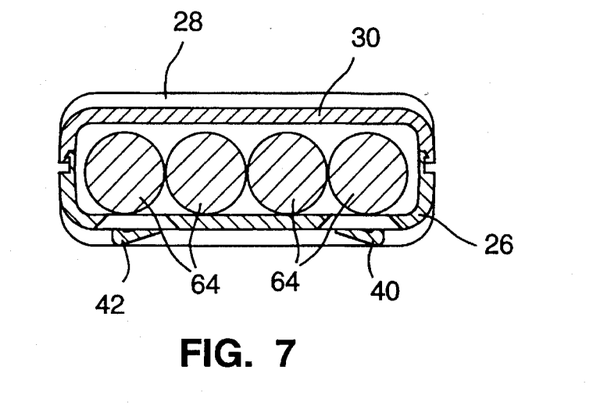
FIG. 7 is a cross-sectional view of the anti-snore apparatus shown in FIG. 2 taken along line 7—7.
Figure 8:
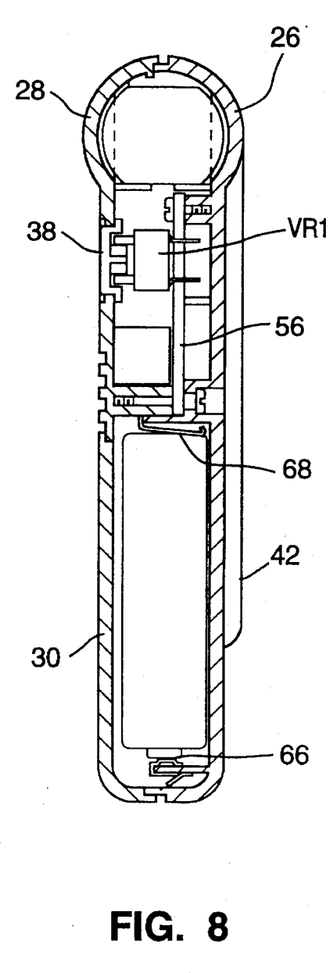
FIG. 8 is a cross-sectional view of the anti-snore apparatus shown in FIG. 2 taken along line 8—8.
Figure 9:
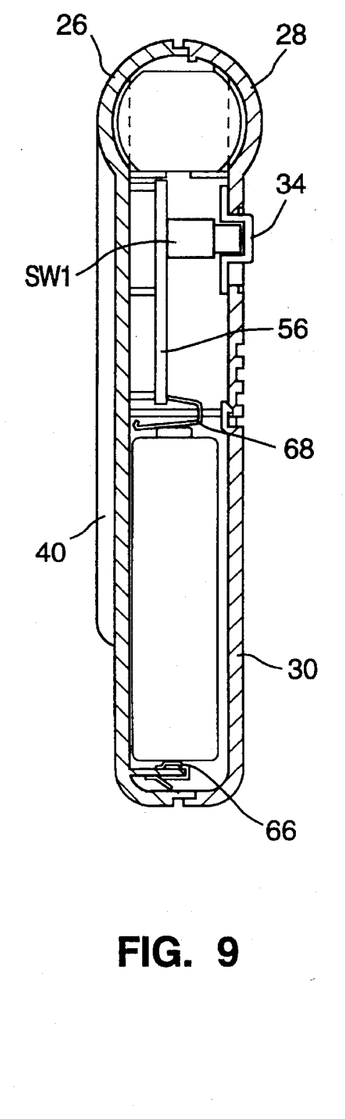
FIG. 9 is a cross-sectional view of the anti-snore apparatus shown in FIG. 2 taken along line 9—9.

Referring to FIGS. 5 and 6A, two clips 40 and 42 are molded to the bottom cabinet 26 to receive a strap 44, or other suitable means, for securing the housing 32 to the person 24. The housing 32 is preferably secured to one of the person's limbs, more preferably, to his or her arm in the vicinity of his or her wrist 22. The housing 32 may, however, be secured to any portion of the person's 24 body. The strap 44 is preferably a 2.0" wide nylon strap. The strap 44 may be secured around the person's wrist 22 in a number of ways. For example, a buckle 45 with a small strap 47 may be used, or, referring to FIG. 6B, a strip of hook fastening material 46 may be placed at one end of the strap 44 and a strip of loop fastening material 48 may be placed at the other end. The strip of hook fastening material 46 and the strip of loop fastening material 48 are preferably the type of hook and loop fastening material, respectively, that is marketed under the trademark VELCRO. Although the buckle 45 or VELCRO fastening material are preferred, other types of fastening devices can be used to secure the strap 44, such as snaps.

Referring to FIGS. 6A through 10, the vibration in the housing 32 is provided by an electric motor 50 that is secured to and contained within the housing 32. Mechanical padding is preferably placed between the motor 50 and the housing 32. A weight 52 is secured to the output shaft 54 of the motor 50. The output shaft 54 extends through the weight 52 at a point outside of the center of gravity of the weight 52 so that rotation of the weight 52 by the output shaft 54 produces a vibratory motion in the housing 32. Although the motor 50 and weight 52 combination is the preferred means of vibration, it should be understood that many different vibrating devices may be mounted in the housing 32 in accordance with the present invention.

Figure 10:
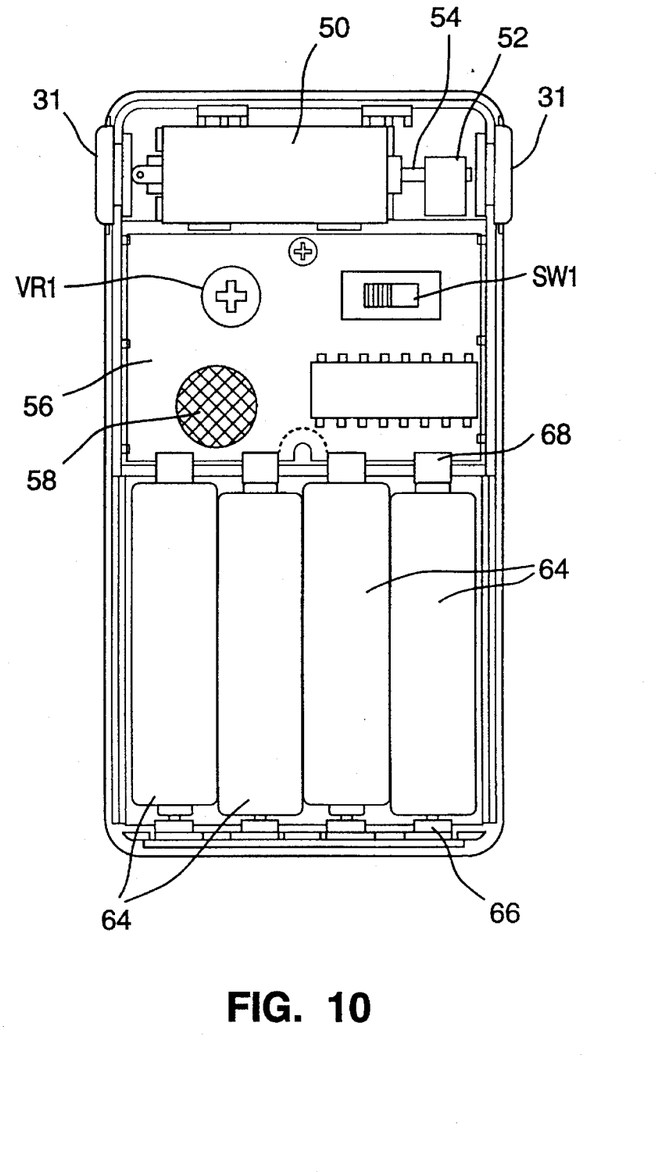
FIG. 10 is a front plan view of the anti-snore apparatus shown in FIG. 1 with the top cabinet and battery door removed.

The electronics which controls the motor 50 is mounted on a printed circuit board (PCB) 56 inside the housing 32 below the top cabinet 28. A microphone 58 for detecting audible snoring is mounted in close proximity to the PCB 56. The microphone 58 should be positioned just below the hole 36 in the top cabinet 28. The microphone 58 is preferably an electret microphone.

A variable resistor VR1 is mounted on the PCB 56 to implement the sensitivity control 38, and an on/off single-pole double-throw switch SW1 is mounted on the PCB 56 below the switch cover 34 to switch the apparatus 20 on and off. The single-pole double-throw switch SW1 is wired as a single-pole single-throw switch. Although a single-pole single-throw switch will perform adequately, a single-pole double-throw switch, or, alternatively, a double-pole double-throw switch, is preferably used for the switch SW1 because these switches provide increased mechanical stability.

While many different types and combinations of battery sizes may be used to power the apparatus 20, there are preferably four "AAA" size batteries 64 wired to provide 6 Volts to the electronics. The batteries 64 are preferably positioned side-by-side within the housing 32 below the battery door 30. Standard battery terminals 66 and 68 may be used to transfer power from the batteries 64 to the PCB 56.

Figure 11:
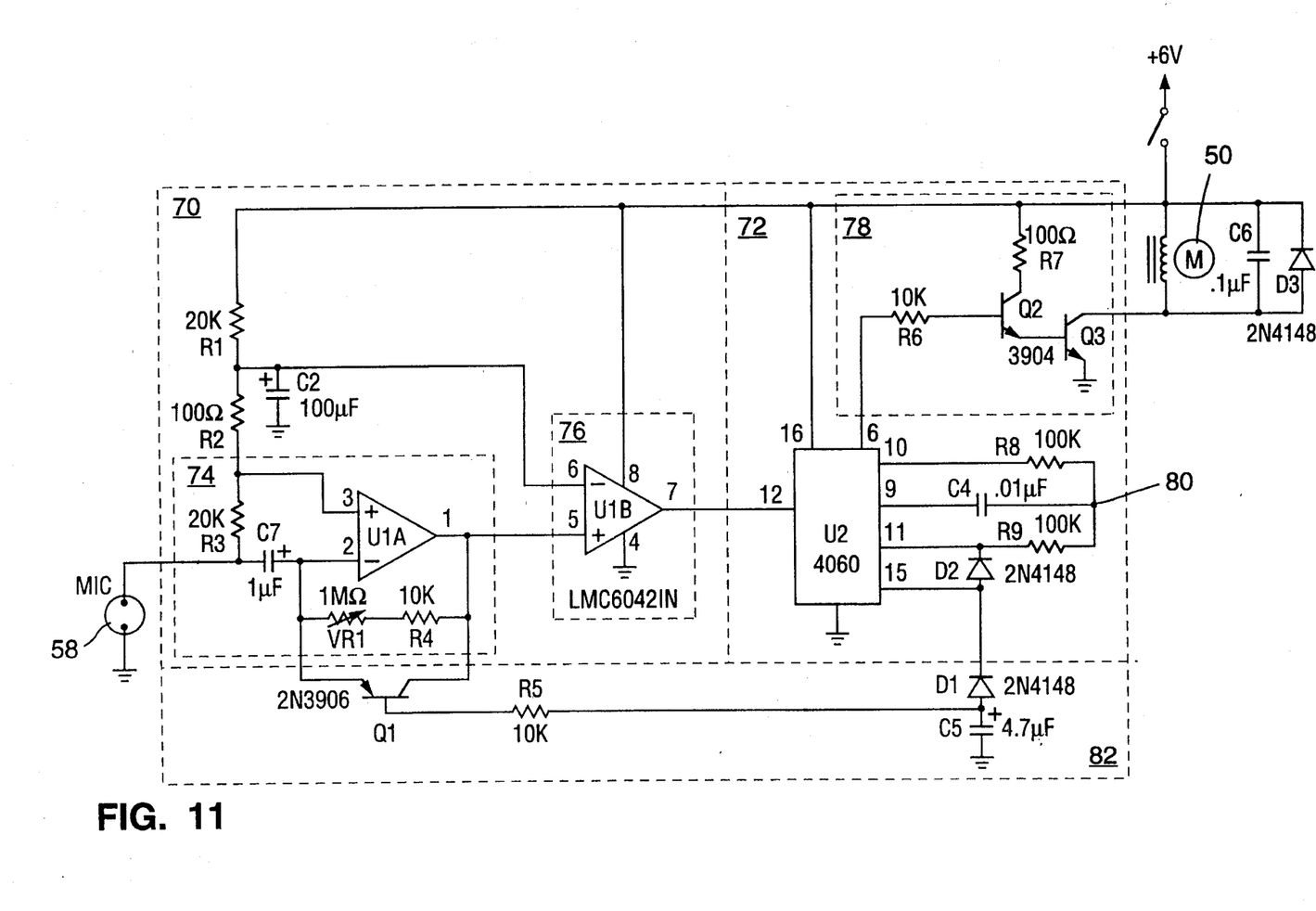
FIG. 11 is a schematic diagram of the electronics contained in the anti-snore apparatus shown in FIG. 1.

Referring to FIG. 11, the electronics of the apparatus 20 includes an input circuit 70 and an output circuit 72. The input circuit 70 determines whether the microphone 58 output signal has exceeded a predetermined level of snoring. The output circuit 72, which is responsive to the input circuit 70, activates the motor 50 when the microphone 58 output signal has exceeded the predetermined level. The circuitry will operate with a 4 to 15 Volt supply and draws quiescently about 200 µA at approximately 6 Volts.

The input circuit 70 includes an audio amplifier 74 and a comparator 76. The audio amplifier 74 amplifies the microphone 58 output signal to produce an amplified microphone output signal, and the comparator 76 produces a comparator output signal in response to the amplified microphone output signal exceeding an amplified predetermined level.

The audio amplifier 74 includes an operational amplifier U1A that employs negative feedback to amplify the microphone 58 output signal. Specifically, a 20 KΩ resistor R1, a 200 Ω resistor R2, and a 20 KΩ resistor R3 are connected in series between the 6 Volt supply and one output of the microphone 58. The same output of the microphone 58 is coupled through a 1.0 µ Farad (Fd) electrolytic capacitor C1 to the inverting input of the operational amplifier U1A. The other output of the microphone 58 is grounded. The noninverting input of the operational amplifier U1A is connected to the node between the resistors R2 and R3. The resistors R1, R2 and R3 set the reference voltage for the operational amplifier U1A (as well as the operational amplifier U1B, discussed below) and furnish bias current for the microphone 58.

The output of the operational amplifier U1A is fed back to its inverting input through a 10 KΩ resistor R4 and the 1 MΩ variable resistor VR1. As mentioned above, the variable resistor VR1 is used to adjust the sensitivity of the apparatus 20, i.e., set the predetermined level of snoring that will activate the motor 50. Sensitivity is adjusted because the variable resistor VR1 adjusts the gain of the operational amplifier U1A. As will be discussed in more detail below, when the gain is very high, the predetermined level of snoring that will activate the motor 50 is very low such that very quiet snores may exceed that level and activate the motor 50. On the other hand, when the gain is very low, the predetermined level of snoring that will activate the motor 50 is higher and louder snores are required to activate the motor 50.

The comparator 76 includes an operational amplifier U1B that is connected in open loop. Specifically, the inverting input of the operational amplifier U1B is connected to the node between the resistors R1 and R2, as well as to a 100 µFd electrolytic capacitor C2. The capacitor C2 provides isolation for the microphone 58 and the resistors R1, R2, and R3. This isolation is needed when the batteries 64 are low. The noninverting input of the operational amplifier U1B is connected to the output of the operational amplifier U1A. The comparator output signal is produced at the output of the operational amplifier U1B.

By way of example, the operational amplifiers U1A and U1B may be model LMC6042IN operational amplifiers manufactured by National Semiconductor Corporation of Santa Clara, Calif. Furthermore, the resistors R1, R2, R3, and R4, as well as the resistors R5, R6, R7, R8, and R9, discussed below, are all 5% tolerance resistors.

The output circuit 72 includes motor circuitry 78 and a counter/oscillator U2. The function of the motor circuitry 78 is to ground the motor 50 in order to switch it on. The motor circuitry 78 includes a one-half ampere npn transistor Q3 having its collector connected to the motor 50 and its emitter grounded. The base of the transistor Q3 is connected to the emitter of a number 2N3904 npn transistor Q2. The collector of the transistor Q2 is coupled through a 100 Ω resistor R7 to the 6 Volt supply. The base of the transistor Q2 is coupled through a 10 KΩ resistor R6 to the counter/oscillator U2. It should be understood that the transistor Q2 is optional and that the base of the transistor Q3 could be connected directly to the resistor R6.

The function of the counter/oscillator U2 is to activate the motor circuitry 78 in order to switch the motor 50 on and off in response to the comparator 76 output signal. The counter/oscillator U2 should be a device or combination of devices which, in response to the comparator 76 output signal, activates the motor circuitry 78 to either switch the motor 50 on for a certain period of time or switch the motor 50 on and off according to a certain combination of on and off cycles. In other words, the counter/oscillator U2 may be designed to control the motor 50 to generate a variety of different vibratory motions in the housing 32. For example, if the motor 50 is switched on for a certain period of time and then switched off, one constant vibratory motion is generated. On the other hand, if the motor 50 is quickly switched on and off several times, a pulsating vibratory motion is generated.

It is believed that some type of pulsating vibratory motion provides the best therapy to "nudge" or induce a sleeping, snoring person to change sleeping positions to stop snoring. Thus, the counter/oscillator U2 is designed to generate an oscillator output signal that is characterized by several voltage pulses that are used to activate the motor circuitry 78 to switch the motor 50 on and off a several times within a short period of time. Specifically, the counter/oscillator U2 will generate four voltage pulses at pin 6 in approximately 1.0 seconds which will switch the motor 50 on and off four times in approximately 1.0 seconds.

By way of example, the counter/oscillator U2 may be a model CD4060 14-Stage Ripple Carry Binary Counter manufactured by National Semiconductor of Santa Clara, Calif. Pins 9, 10, and 11 of the counter/oscillator U2 control the oscillator section. In order to generate four pulses in about 1.0 seconds at pin 6, a 0.01 µFd mylar capacitor C4 is connected between pin 9 and a node 80, a 100 KΩ°resistor R8 is connected between pin 10 and the node 80, and a 100 KΩ resistor R9 is connected between pin 11 and the node 80. Furthermore, a number 2N4148 small signal diode D2 is connected between pin 15 and pin 11. Pin 6 is coupled through the 10 KΩ resistor R6 to the base of the transistor Q2 in the motor circuitry 78.

A disabling circuit 82 is coupled between the output circuit 72 and the input circuit 70. The function of the disabling circuit 82 is to disable the audio amplifier 74 while the motor 50 is switched on so that noise generated by the motor 50 is not "heard" by the microphone 58 so as to retrigger the oscillator U2. The disabling circuit 82 achieves this function by reducing the gain of the audio amplifier 74 to approximately zero.

The disabling circuit 82 includes a number 2N3906 pnp transistor Q1 having its emitter coupled to the inverting input of the operational amplifier U1A and its collector coupled to the output of the operational amplifier U1A. The base of the transistor Q1 is coupled through a 10 KΩ resistor R5 to the anode of a 4.7 µFd electrolytic capacitor C5. The anode of the capacitor C5 is coupled through a number 2N4148 small signal diode D1 to pin 15 of the oscillator U2, and the cathode of the capacitor C5 is grounded.

The motor 50 preferably has a 0.1 µFd ceramic capacitor C6 coupled across its terminals in order to keep motor noise out of radios. Furthermore, a number 2N4148 small signal diode D3 is also coupled across the motor 50 terminals in order to protect the transistor Q3 from inductive kick.

In order to operate the apparatus 20, a user switches the on/off switch SW1 to the on position. The 6 Volt supply is applied across the resistors R1, R2 and R3 to set the reference voltage for the operational amplifiers U1A and U1B and to furnish bias current for the microphone 58. When the switch SW1 is switched to the on position, the motor 50 runs for one-cycle, i.e., four quick pulses, to let the user know that the unit has been switched on.

When the motor 50 is not running, the transistor Q1 is in the nonconducting state which leaves the operational amplifier U1A active. The operational amplifier U1A amplifies the output of the microphone 58. The capacitor C1 blocks direct current from the resistors R1, R2, and R3 and permits only the output signal of the microphone 58 to be amplified.

The gain, i.e, the sensitivity, of the operational amplifier U1A is adjusted by the variable resistor VR1. By adjusting the variable resistor VR1 the user can set the predetermined level of snoring that will activate the counter/oscillator U2. The resistance of the variable resistor VR1 changes linearly which corresponds to the gain changing linearly. Although the linear variable resistor VR1 functions adequately, a log taper may be used for VR1 to make the gain of the operational amplifier U1A reasonably linear with respect to the sensitivity control 38 knob.

The output of the operational amplifier U1A is DC coupled to the operational amplifier U1B that is connected to form the comparator 76. The resistor R2 sets the differential voltage of the operational amplifier U1B. When no snoring is present, the inverting and noninverting inputs of the operational amplifier U1B are nearly equal because the output voltage of the operational amplifier U1A is equal to the voltage at its noninverting input. With the inverting and noninverting inputs of the operational amplifier U1B nearly equal, its output remains low and the counter/oscillator U2 is not triggered.

When detectable audible snoring occurs, the microphone 58 output is amplified by the operational amplifier U1A. If the snoring is loud enough, i.e., above the predetermined level as set by the variable resistor VR1, the amplification by the operational amplifier U1A causes the voltage at the noninverting input of the operational amplifier U1B to go above the voltage present at the inverting input of the operational amplifier U1B. The higher the gain of the operational amplifier U1A (as set by the variable resistor VR1), the quieter the snore can be which will cause the voltage at the noninverting input of the operational amplifier U1B to go above the voltage present at the inverting input of the operational amplifier U1B. Because of the difference in the voltages present at the inverting and noninverting inputs of the operational amplifier U1B, the output of the operational amplifier U1B, i.e., the comparator 76 output signal, resets the counter/oscillator U2 via pin 12.

When the counter/oscillator U2 is reset, pin 15 goes low which releases the oscillator section of the counter/oscillator U2, i.e., pins 9, 10 and 11. In addition, when pin 15 goes low, the disabling circuit 82 is activated. Specifically, the capacitor C5 is discharged which pulls down the base of the transistor Q1 such that it is switched into the conducting state. Because the transistor Q1 is in the conducting state, the inverting input and output of the operational amplifier U1A is shorted which decreases its gain towards zero and essentially shuts down the operational amplifier U1A. Because the operational amplifier U1A is temporarily not amplifying, the noise created by the motor 50 and detected by the microphone 58 will not retrigger the counter/oscillator U2.

When the counter/oscillator U2 is reset by the comparator 76 output signal, the oscillator output signal is generated at pin 6 of the counter/oscillator U2. The oscillator output signal is characterized by four voltage pulses as described above. The first pulse of the oscillator output signal switches the transistor Q2 into the conducting state. When the transistor Q2 is in the conducting state, the transistor Q3 also switches into the conducting state which switches the motor 50 on. At the end of the first pulse of the oscillator output signal the transistors Q2 and Q3 switch off which switches the motor 50 off. The transistors Q2 and Q3 and the motor 50 are switched on and off three more times before pin 15 again goes positive. Thus, the counter/oscillator U2 generates 4 cycles at pin 6 to switch the transistors Q2 and Q3 and the motor 50 on and off 4 times.

At the end of the oscillator output signal, i.e., after the motor 50 has switched on and off four times, pin 15 of the counter/oscillator U2 goes high. This switches the oscillator section off which pulls pin 6 low and leaves the motor 50 off. Furthermore, the anode of the diode D1 goes high which causes the capacitor C5 of the disabling circuit 82 to charge up through the resistor R5. After approximately 0.5 seconds, the capacitor C5 begins to be charged up by the leakage current of the transistor Q1 which begins to pull the base of the transistor Q1 high. The transistor Q1 is switched into the nonconducting state after approximately 10 or more seconds. After the approximately 10 or more seconds, the audio amplifier 74 is restored to its maximum set gain when the transistor Q1 is in the nonconducting state. When the transistor Q1 is in the nonconducting state the operational amplifier U1A is restored and snoring can again retrigger the counter/oscillator U2. The approximately 10 or more second delay insures that the residual noise from the motor 50 is gone before the audio amplifier 74 is turned back on. Furthermore, the delay insures that noise made by the snoring person in adjusting or rolling to a different sleeping position does not retrigger the counter/oscillator U2. The delay is controlled by the values of the capacitor C5 and the base current of the transistor Q1.

As mentioned above, the variable resistor VR1 adjusts the gain, and thus the sensitivity, of the operational amplifier U1A. Maximum gain, i.e., maximum sensitivity, occurs when the variable resistor VR1 is set for its full 1 MΩ resistance. At maximum gain the predetermined level of snoring that will activate the counter/oscillator U2 is low such that quiet snores will activate the counter/oscillator U2. Minimum gain, i.e., minimum sensitivity, occurs when the variable resistor VR1 is set for zero resistance. When the variable resistor VR1 is set for zero resistance, the total resistance of the feed back loop of the operational amplifier U1A is only 10 KΩ, i.e., the value of the resistor R4. Therefore, when the variable resistor VR1 is set for zero resistance, the gain of the operational amplifier U1A is approximately 1% of the maximum gain and the predetermined level of snoring that will activate the counter/oscillator U2 is high. It follows that the range of the sensitivity control 38, i.e., the variable resistor VR1, is 100 to 1 (at about 100 Hz, as will be discussed below) which gives the user a wide sensitivity range.

Figure 12A:
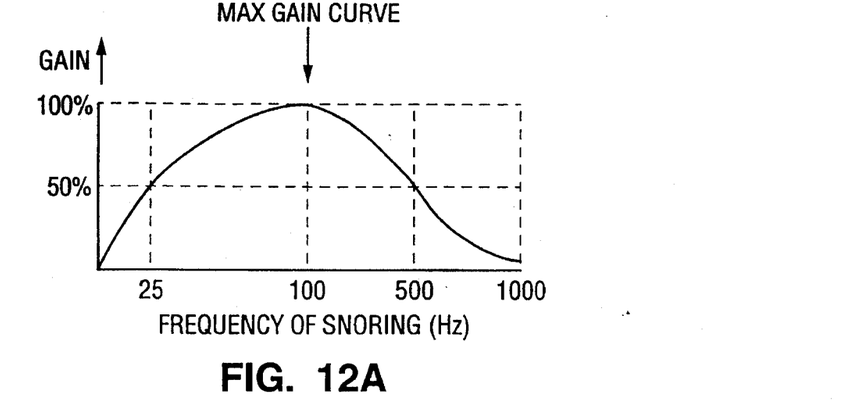
FIGS. 12A through 12C are frequency response diagrams for the anti-snore apparatus shown in FIG. 1.
Figure 12B:
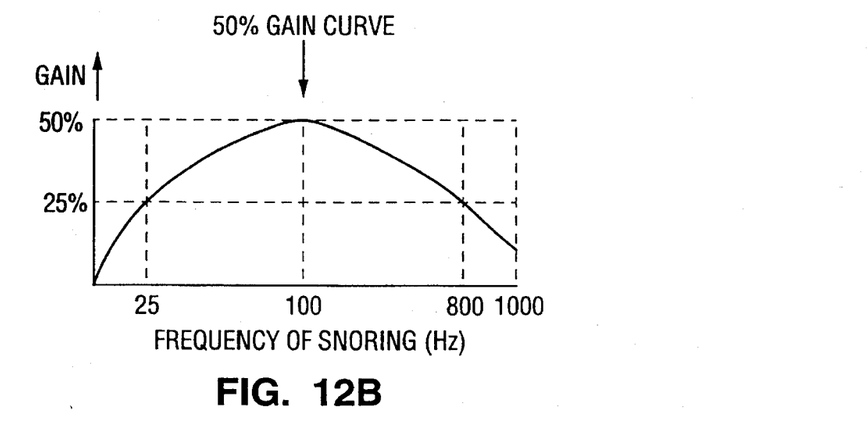
Figure 12C:
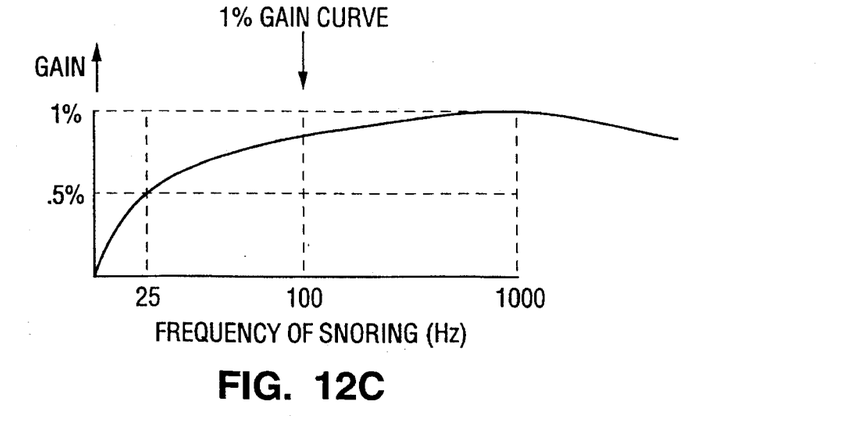

FIGS. 12A, 12B, and 12C illustrate the frequency response of the operational amplifier U1A when the variable resistor VR1 is set for maximum gain, 50% gain, and 1% gain, respectively. The low frequency response is controlled by the value of the capacitor C1. If the value of the capacitor C1 is increased the apparatus 20 is more sensitive to lower frequency sounds.

As shown in FIG. 12A, when the variable resistor VR1 is set for maximum gain the operational amplifier U1A is most sensitive to sounds having a frequency of approximately 100 Hz. The sensitivity of the operational amplifier U1A drops quickly for sounds having frequencies above 500 Hz. It is believed that the frequency of audible snoring typically falls in the range of approximately 100 Hz to 900 Hz. Therefore, the operational amplifier U1A is sensitive to lower frequency snoring but is not sensitive to higher frequency sounds, such as the rustling of bed sheets. This attempts to insure that mainly snoring sounds will activate the counter/oscillator U2.

Referring to FIG. 12B, when the variable resistor VR1 is set for 50% gain the sensitivity of the operational amplifier U1A increases slightly for higher frequency sounds. However, the operational amplifier U1A is still most sensitive to sounds having a frequency of approximately 100 Hz, and, because the overall gain is only 50%, the operational amplifier U1A is still not very responsive to high frequency sounds.

Referring to FIG. 12C, when the variable resistor VR1 is set for minimum gain the operational amplifier U1A is sensitive to high frequency sounds. However, because the gain is only 1%, the operational amplifier U1A is responsive to only very loud sounds. Therefore, one can conclude from the curves shown in FIGS. 12A through 12C that the high frequency response of the apparatus 20 decreases rapidly as the gain of the operational amplifier U1A is increased and that the apparatus 20 is very sensitive to lower audio frequencies at maximum gain.

As mentioned above, the frequency of audible snoring typically falls in the range of approximately 100 Hz to 900 Hz. While a person's snoring may have a frequency as high as 900 Hz, the apparatus 20 is most sensitive to low frequency snoring. For example, at maximum gain the apparatus 20 is most sensitive to 100 Hz snoring but is also fairly sensitive to snoring falling in the range of 25 Hz to 500 Hz, and at 50% gain the apparatus 20 is still most sensitive to 100 Hz snoring but will still detect snoring falling in the range of 25 Hz to 800 Hz. As alluded to above, the reason for detecting lower frequency snoring is to prevent higher frequency sounds from falsely triggering the counter/oscillator U2. Other noises that are made while sleeping, such as rolling over and rustling bed sheets, can have frequency ranges that overlap with the high end of the snoring frequency range. By detecting mostly the lower end of the snoring frequency range, false triggering of the counter/oscillator U2 by these other noises is largely prevented.

The apparatus 20 performs a method that is believed to be effective to "nudge", induce, or cause a sleeping, snoring person to change sleeping positions in order to sleep without snoring. The method basically includes the steps of detecting the sound of a person's snoring and then, if the detected snoring exceeds a predetermined level, applying vibratory motion to the person. Preferably, snoring sounds having frequencies falling in the range of approximately 25 Hz to 900 Hz are detected before other frequency sounds, with approximately 75 Hz to 150 Hz being the most sensitive snoring frequency. The vibratory motion is preferably applied to one of the person's limbs, particularly his or her arm in the vicinity of his or her wrist. The duration, number, and types of vibratory motions applied to the person may be of many different forms. As discussed above, it is believed that four quick applications of vibration to the person's wrist in a period of approximately 1.0 seconds is effective to stop the person from snoring. However, it should be well understood that the specific manner and location in which the vibration is applied may be varied without departing from the scope of the present invention.

As discussed above, the oscillator section of the counter/oscillator U2 is controlled by pins 9, 10, and 11. With the settings shown in FIG. 11, the motor 50 switches on and off four times in about 1.0 seconds. The duration of the voltage pulses in the oscillator output signal at pin 6 is set by the values of the resistor R8 and the capacitor C4. By adjusting these values the output "power" of the apparatus 20, i.e., how quickly the motor 50 switches on and off, can be adjusted.

Figure 13:
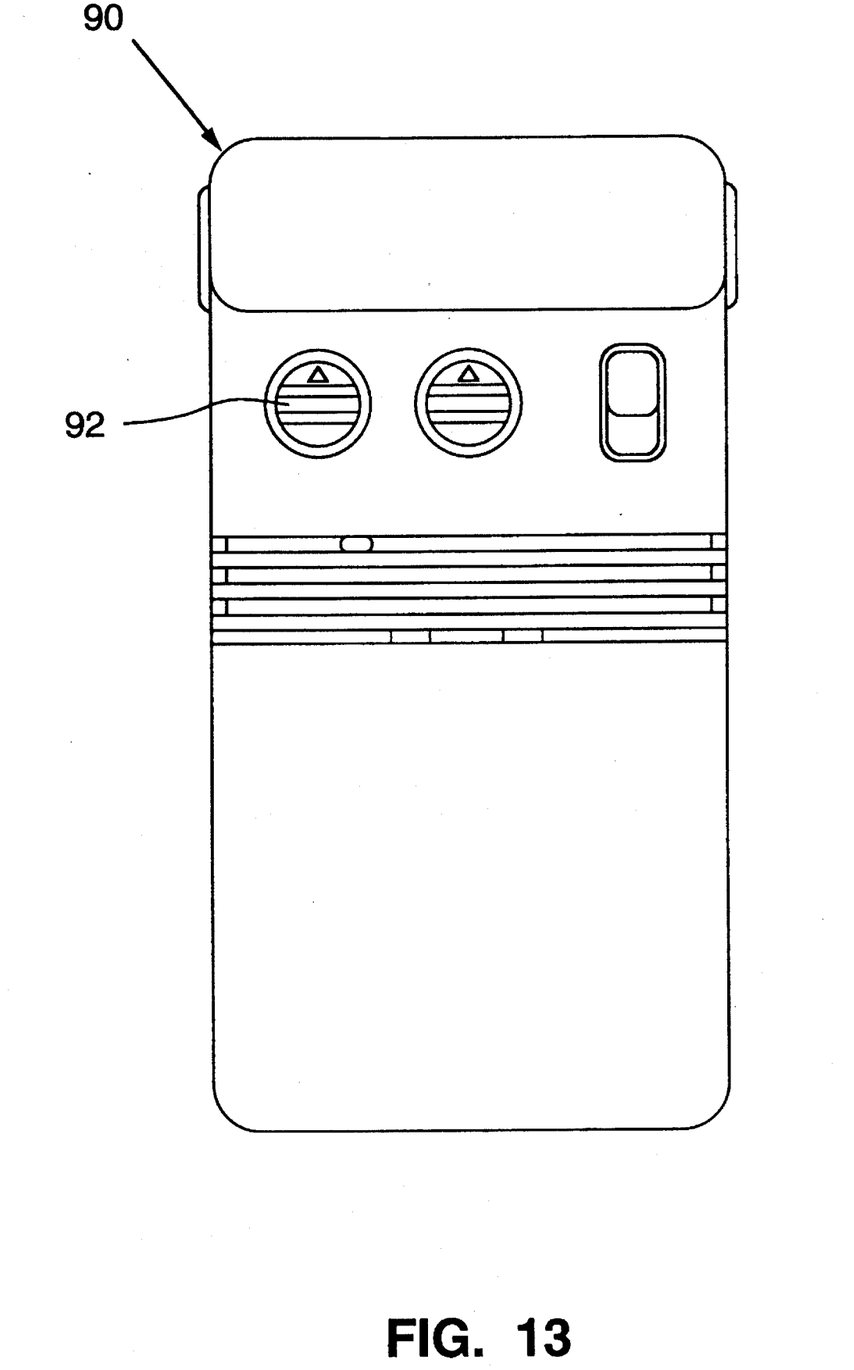
FIG. 13 is a front view of another embodiment of an anti-snore apparatus in accordance with the present invention.

The power of the apparatus 20 can be made easily adjustable if a variable resistor is substituted for the resistor R8. Referring to FIG. 13, there is illustrated an alternative embodiment of an anti-snore apparatus 90 in accordance with the present invention. The apparatus 90 is substantially identical to the apparatus 20 except for the inclusion of a power control 92. The power control 92 allows a user to adjust how rapidly the four vibrations occur.

Figure 14:
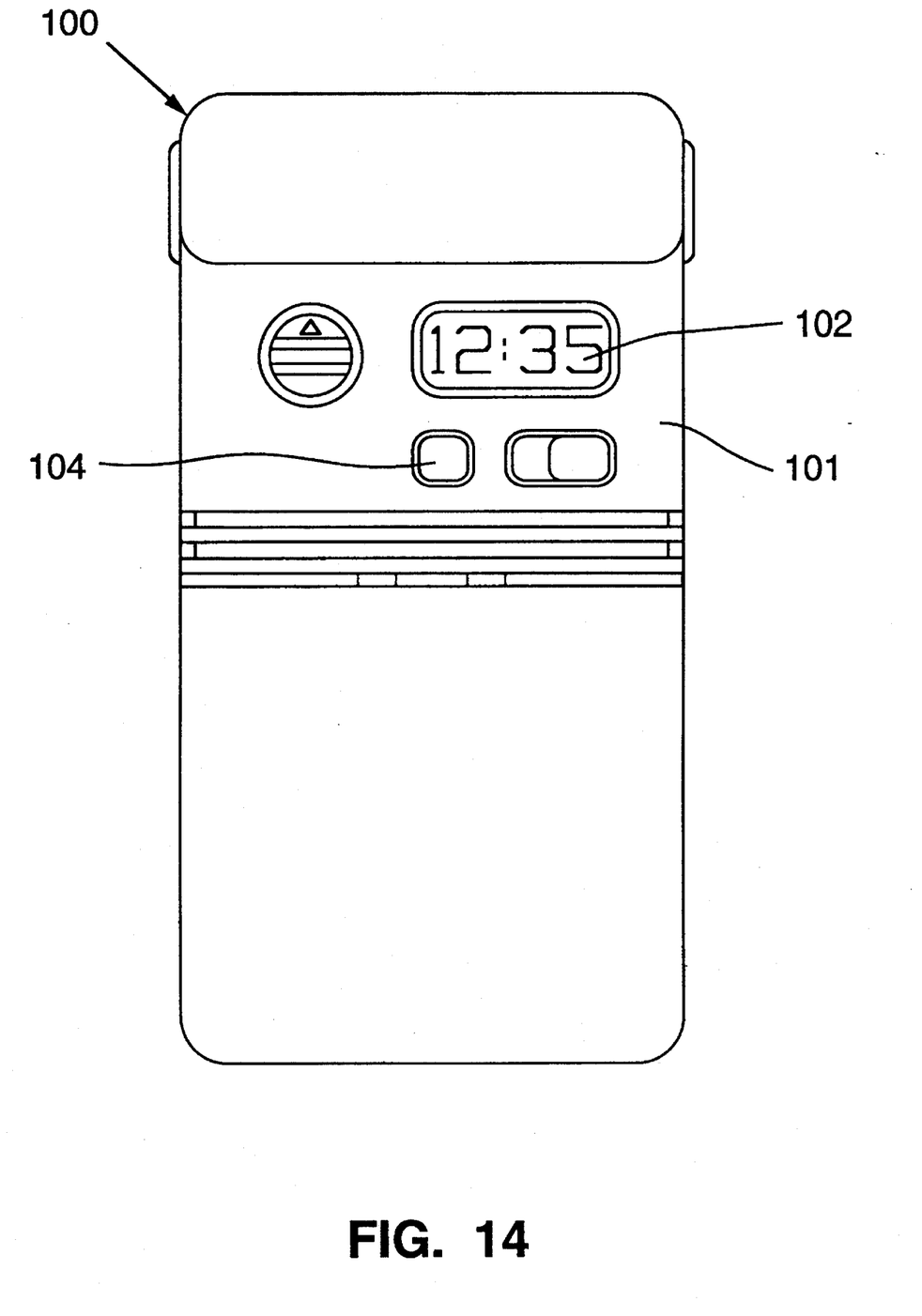
FIG. 14 is a front view of another embodiment of an anti-snore apparatus in accordance with the present invention.

Referring to FIG. 14:, there is illustrated an alternative embodiment of an anti-snore apparatus 100 in accordance with the present invention. The apparatus 100 is substantially identical to the apparatus 20 except for the inclusion of a clock 102. The clock 102 allows the apparatus 100 to also be used as a wake-up device, i.e., an alarm clock. The clock 102 is preferably an LCD type clock and is mounted in the top cabinet 101 of the housing. A clock control 104 is used to set the time and alarm of the clock 102. The clock 102 preferably uses the motor 50, i.e., vibration, as the alarm. Alternatively, an audio alarm may be added to the apparatus 100.

Figure 15:
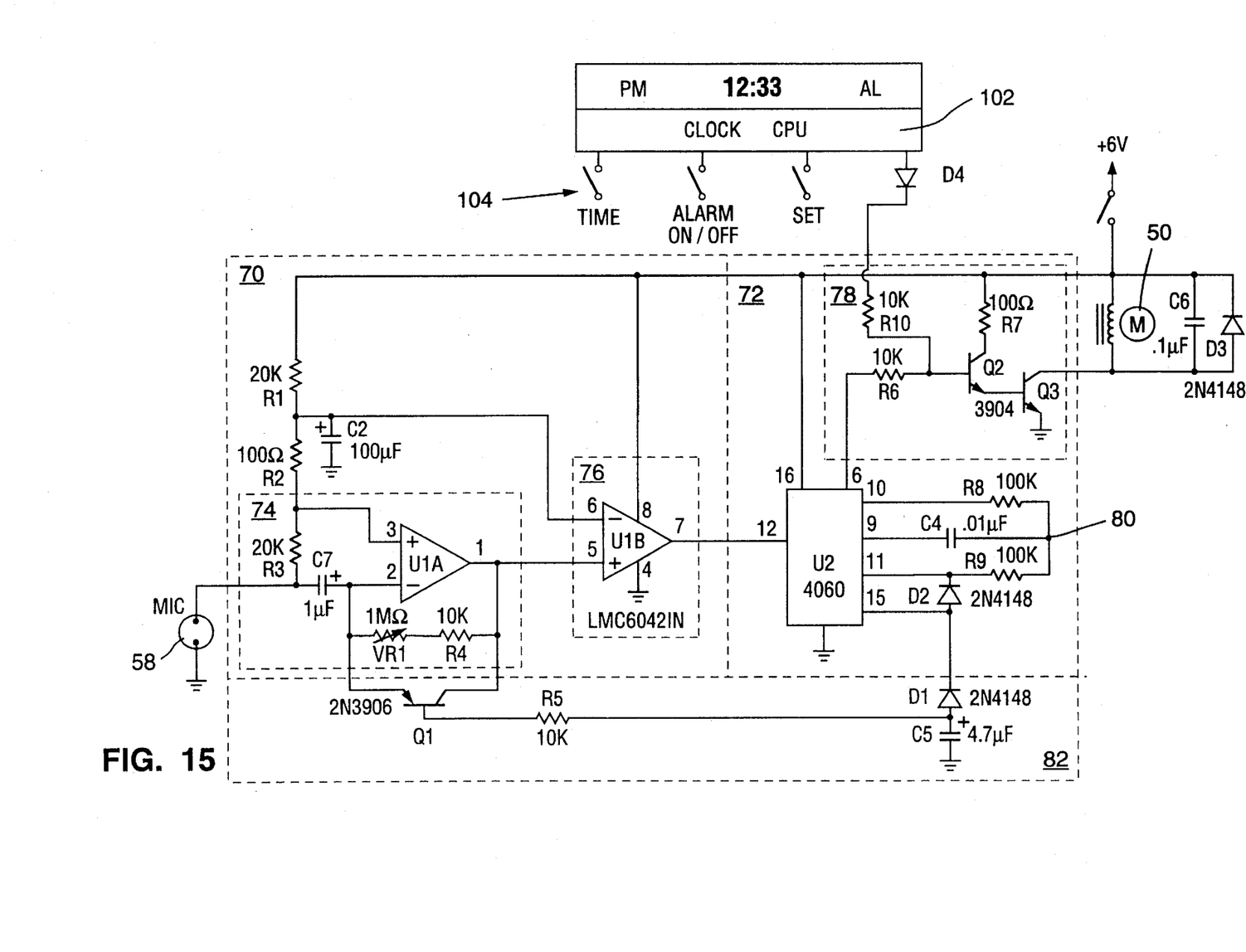
FIG. 15 is a schematic diagram of the electronics contained in the anti-snore apparatus shown in FIG. 14.

Referring to FIG. 15, the alarm output of the clock 102 is connected through a number 2N4148 small signal diode D4 and a 10 KΩ resistor R10 to the base of the transistor Q2. When the alarm activates, the transistors Q2 and Q3 switch into the conducting state which causes the motor 50 to switch on. The motor 50 runs continuously until the constant vibration wakes the user up and the user switches the alarm off via the clock control 104. The clock control 104 includes time set, alarm on/off, and alarm set controls.

In an alternative embodiment, the clock 102 could be connected to the counter/oscillator U2 so that the same type of pulsating vibration described above occurs when the alarm activates. If the alarm output of the clock 102 is connected to pin 12 of the counter/oscillator U2, activation of the alarm will cause the same four quick vibrations discussed above. Circuitry could be added, however, to disconnect the diode D2 which would cause the motor 50 to continuously pulsate. Furthermore, circuitry could be added to cause the motor 50 to pulsate or run continuously for a certain period of time, e,g,, one minute, and then shut off automatically in order to conserve battery power.

It should be understood that various alternatives to the embodiments of the invention described herein may be employed in practicing the invention. It is intended that the following claims define the scope of the invention and that structures and methods within the scope of these claims and their equivalents be covered thereby.

What is claimed is:

1. An anti-snore apparatus, comprising:

a housing that is wearable on a person's limb;

a strap having each end thereof attachable to the housing for securing the housing to a person's limb;

means contained within the housing for receiving a power supply;

a motor secured to and contained within the housing;

a weight secured to an output shaft of the motor, the output shaft extending through the weight at a point outside of a center of gravity of the weight so that rotation of the weight by the output shaft produces a vibratory motion in the housing;

a microphones contained within the housing and positioned near a hole in the housing, that detects audible snoring and that produces a microphone output signal in response to such detected snoring;

an audio amplifier having a gain that amplifies the microphone output signal to produce an amplified microphone output signal;

a comparator that produces a comparator output signal in response to the amplified microphone output signal exceeding a predetermined level;

an oscillator, responsive to the comparator output signal, that generates an oscillator output signal characterized by a plurality of voltage pulses which successively switch the motor on and off a plurality of times to create a pulsating vibratory motion in the housing, and means for disabling the audio amplifier while the motor is switched on.

2. An apparatus according to claim 1, wherein the audio amplifier primarily only amplifies snoring sounds having a frequency of less than or equal to 900 Hz.

3. An apparatus according to claim 1, wherein the audio amplifier comprises:
   a first operational amplifier having its inverting output coupled through a capacitor to the microphone; and
   a variable resistor coupled between the inverting input and the output of the first operational amplifier that adjusts the gain of the audio amplifier.

4. An apparatus according to claim 1, wherein the comparator comprises:
   a second operational amplifier having its non-inverting input coupled to the output of the first operational amplifier and its output coupled to the oscillator.

5. An apparatus according to claim 1, further comprising:
   a first transistor, responsive to the oscillator output signal, that switches the motor on and off.

6. An apparatus according to claim 1, wherein the means for disabling comprises:
   a second transistor that reduces the gain of the audio amplifier to approximately zero;
   a capacitor coupled to the base of the second transistor and to the oscillator that switches the second transistor into a conducting state while the motor is running.

7. An apparatus according to claim 1, further comprising:
   a clock mounted in the housing, the clock having an alarm output that is connected to activate the motor.

* * * * *